United States Patent [19] [11] 3,984,463
Pilgram [45] Oct. 5, 1976

[54] HERBICIDAL 2-PHENYL SEMICARBAZIDES
[75] Inventor: Kurt H. G. Pilgram, Modesto, Calif.
[73] Assignee: Shell Oil Company, Houston, Tex.
[22] Filed: May 20, 1974
[21] Appl. No.: 471,380

Related U.S. Application Data
[63] Continuation-in-part of Ser. No. 445,396, Feb. 25, 1974, abandoned, which is a continuation of Ser. No. 283,687, Aug. 25, 1972, abandoned.

[52] U.S. Cl. ............................ 260/501.17; 71/121; 260/501.19; 260/501.2; 260/501.21; 260/554
[51] Int. Cl.² ................................... C07C 133/02
[58] Field of Search ......... 260/544, 501.17, 501.19, 260/501.2, 501.21; 71/121

[56] References Cited
FOREIGN PATENTS OR APPLICATIONS
7,110,689  1/1972  Netherlands
1,191,924  5/1970  United Kingdom OTHER PUBLICATIONS
"Hydrolysis of Steroid Semicarbazones With Concentrated Hydrochloric Acid", Pancrazio et al., CA 50: 13975b (1956).

Primary Examiner—Daniel E. Wyman
Assistant Examiner—Thomas A. Waltz

[57] ABSTRACT
2-Phenylsemicarbazides of the formula

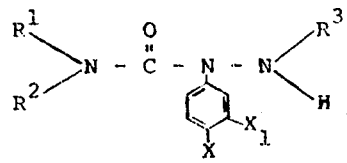

where $R^1$, $R^2$ and $R^3$ are hydrocarbyl, X is hydrogen or halogen and $X_1$ is halogen, alkyl or alkoxy optionally substituted by halogen, useful as herbicides, are prepared by treatment of the appropriately substituted 2-phenylsemicarbazone with an aqueous acid followed by treatment with a base and optionally further an alkylating or acylating agent.

5 Claims, No Drawings

HERBICIDAL 2-PHENYL SEMICARBAZIDES

CROSS-REFERENCE TO RELATED APPLICATIONS

This application is a continuation-in-part of Ser. No. 445,396 filed Feb. 25, 1974 which is a continuation of Ser. No. 283,687 filed Aug. 25, 1972, both now abandoned.

BACKGROUND OF THE INVENTION

1. Field of the Invention

This invention relates to new herbicides and to herbicidal compositions containing said herbicides. More specifically, this invention relates to a new class of 2-phenylsemicarbazides and the acid addition salts thereof, a new method for preparation of said 2-phenylsemicarbazides and to a new method for controlling undesirable plant growth using said 2-phenylsemicarbazides.

2. Description of the Prior Art

German Pat. No. 1,926,768 discloses 1,1,4-trimethyl-2-phenyl-4-propylsemicarbazide for use as a fungicide, bactericide, and herbicide. German Pat. No. 1,445,790 discloses 2-phenylsemicarbazide, 2-phenylmethylsemicarbazide, and 2,4-diphenylsemicarbazide for use as intermediates for benzoxazinone derivatives. Netherlands patent application No. 7,010,689 discloses the 2-(3,4-dichlorophenyl)-4,4-dimethylsemicarbazide and 1-alkyl derivatives thereof for use as herbicides.

SUMMARY OF THE INVENTION

The novel compounds of this invention are represented by the formula

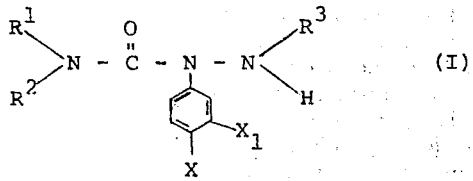

where $R^1$ and $R^2$ are each hydrogen, alkyl, or alkoxy; $R^3$ is hydrogen, alkyl, or acyl of the formula $R^4$—C(=O)—; in which $R^4$ is hydrogen, alkyl, haloalkyl, alkenyl or cycloalkyl;

X is hydrogen or halogen, and $X_1$ is halogen, alkyl or alkoxy wherein the alkyl portion may be substituted by one or more halogens; and acid addition salts thereof.

Acid addition salts of the 2-phenylsemicarbazides of Formula I wherein $R^3$ is hydrogen can be prepared by acid-catalyzed hydrolytic cleavage of the appropriate 2-phenylsemicarbazone.

Herbicidal compositions of this invention comprise a compound within the scope of the invention and an inert, agriculturally acceptable carrier therefor. Undesirable plant growth is destroyed or prevented by applying the compounds of the invention, ordinarily in a herbicidal composition of one of the aforementioned types, to either the unwanted vegetation itself or to the area to be kept free of such unwanted vegetation.

DETAILED DESCRIPTION OF THE INVENTION

Typical novel compounds of this invention are those of Formula I above wherein $R^1$ and $R^2$ are each hydrogen, alkyl of 1 to 4 carbon atoms, for example, methyl, ethyl, isopropyl, tert-butyl, and the like, or alkoxy of 1 to 4 carbon atoms, for example, methoxy, ethoxy, propoxy, and the like; $R^3$ is hydrogen, alkyl of 1 to 4 carbon atoms, or acyl of the formula $Rl^4$—C(=O)— in which $R^4$ is hydrogen, alkyl of 1 to 4 carbon atoms, optionally substituted by one or more halogen of atomic number 9–35, inclusive, that is, fluorine, chlorine, or bromine, alkenyl of 2 to 4 carbon atoms, for example, vinyl, allyl, 2-butenyl, and the like, cycloalkyl of 3 to 7 carbon atoms, for example, cyclopropyl, cyclobutyl, cyclohexyl, and the like; X is hydrogen or is halogen of atomic number 9 to 35 inclusive; $X_1$ is halogen of atomic number 9 to 35 inclusive, alkyl, or alkoxy, wherein the alkyl portion contains 1 to 4 carbon atoms and may be substituted by one or more halogen atoms, for example, trifluoromethoxy, and the like.

The acid addition salts of the above compounds are formed with inorganic or organic acids. Suitable inorganic acids include hydrochloric, hydrobromic, sulfuric, phosphoric and nitric acids. Suitable organic acids include maleic, fumaric citric, tartaric, methanesulfonic, ethanedisulfonic, acetic and benzoic acids.

Typical compounds contemplated for use within the scope of this invention include:

semicarbazide, 1,4,4-trimethyl-2-(3-fluoro-4-chlorophenyl.

semicarbazide, 2-(4-bromo-3-tolyl)-4,4,-dimethyl.

semicarbazide, 2-(3-chloro-4-iodophenyl)-4,4,dimethyl, trichloroacetate.

semicarbazide, 2-(3-chloro-4-bromophenyl)-4,4-dimethyl.

semicarbazide, 1-cyclopropylcarbonyl-4,4-dimethyl-2-(3-trifluoromethyl)phenyl).

semicarbazide, 1-chloroacetyl-4,4-dimethyl-2-(3-trifluoromethyl)phenyl).

semicarbazide, 1-(1,2-dichloro-1-propenoyl)-4,4-dimethyl-2-(3-(trifluoromethoxy)phenyl).

semicarbazide, 1-acetyl-4,4-dimethyl-2-(3,4-dichlorophenyl).

Preferred because of their especially effective herbicidal properties and their ability to control weeds at relatively low dosages are those semicarbazides of Formula I wherein $R^1$ and $R^2$ are each alkyl of 1–4 carbon atoms, $R^3$ is hydrogen, X is hydrogen, chlorine or fluorine, $X_1$ is chlorine, trifluoromethyl, or trifluoromethoxy, and the hydrochloride addition salts thereof.

Typical compounds of this subclass include: 4,4-dimethyl-2-(3-(trifluoromethyl)phenyl)semicarbazide and 2-(3,4-dichlorophenyl)-4,4-dimethylsemicarbazide.

The herbicidal acid addition salts of compounds of Formula I wherein $R^3$ is hydrogen are prepared by acid hydrolysis of the corresponding semicarbazone according to the following reaction:

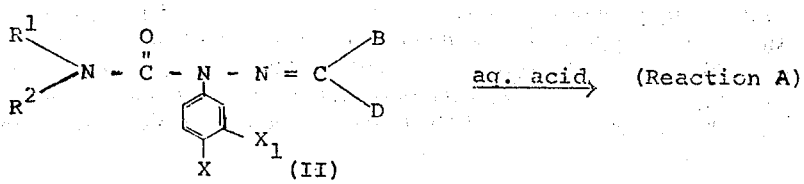

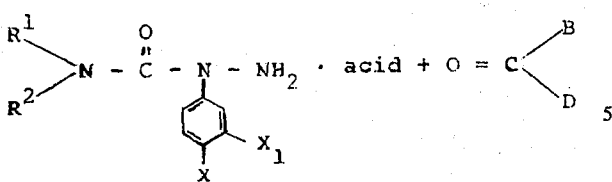 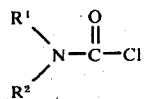

(III)

where B and D each represent any suitable, non-reactive substituent, for example, hydrogen, alkyl, haloalkyl, cycloalkyl, aryl, alkylamino, heteroaromatic radicals. Preferable substituents for the purpose of this invention are hydrogen, alkyl of 1 to 10 carbon atoms, optionally substituted by one or more, preferably one to three, halogen atoms of atomic number 9–35, aryl, such as phenyl, naphthyl, benzyl and the like, heteroaromatic such as pyridyl, furyl, or thienyl, alkylamino, such as methylamino, dimethylamino, diethylamino, and the like, or cycloalkyl such as cyclopentyl, cyclohexyl, and the like. The acid salt thus prepared may be treated with a base to obtain the free semicarbazide which may be acylated or alkylated as desired.

THe semicarbazones, designated by Formula II in the above reaction may be prepared by various methods.

According to one method, phenylhydrazine is treated with a ketone or aldehyde to yield the corresponding phenyl hydrazone. The phenylhydrazone is then treated with phosgene in a non-hydroxylic solvent such as benzene, toluene, xylene, tetrahydrofuran, or ethyl acetate and in the presence of a tertiary base acceptor for the by-product hydrogen chloride to yield an N-(alkylideneamino)carbanilic acid chloride of the formula

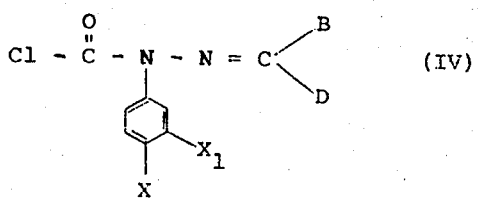 (IV)

which is further treated with ammonia or an amine in the presence of excess amine reagent itself or a tertiary amine such as triethylamine, pyridine, picoline, or collidine, which acts as an acceptor for the hydrogen chloride formed as a by-product of the reaction, to yield the desired semicarbazone.

Alternatively, a phenylhydrazone prepared as above is treated with a strong base, such as sodium hydride, sodium methoxide or butyl lithium, in the solution in a solvent such as dimethylformamide, sulfolane, acetonitrile or dimethyl sulfoxide and then treated with a carbamoyl choride of the formula

to yield the corresponding semicarbazone.

2-Phenylsemicarbazones wherein $R^1$ is alkyl and $R^2$ is hydrogen may be prepared by the reaction of a phenylhydrazone with an alkyl isocyanate, optionally in the presence of a catalyst such as triethylamine.

For a more detailed description of the semicarbazone preparation, see Ser. No. 283,686 filed Aug. 25, 1972, the pertinent disclosure of which is hereby incorporated by reference.

Salts of 2-phenylsemicarbazides of Formula III above wherein $R^1$ and $R^2$ are alkyl or alkoxy and X as defined above prepared as shown in Reaction A. The reaction is carried out at a temperature at which the carbonyl by-product $$\begin{array}{c} B \\ \diagdown \\ C=O \\ \diagup \\ D \end{array}$$

distils as formed. The reaction can be carried out at atmospheric pressure or at super- or sub-atmospheric pressure to adjust the distillation temperature to one suitable for carrying out the reaction. If desired, the carbonyl by-product is recycled for use in the preparation of the starting phenylhydrazone.

The reaction usually proceeds to completion in about 3 to 12 hours; however, variations in the particular reactants and the reaction conditions can lead to significant increases or decreases in the reaction rate.

The 2-phenylsemicarbazides of Formula I wherein $X_1$, $R^1$, $R^2$ and X are as defined above, and $R^3$ is hydrogen, can be prepared by reaction of the salt of Formula III with a base such as ammonium hydroxide, sodium hydroxide, potassium hydroxide, or the like. The desired product is extracted with an inert solvent, for example, diethyl ether, and separated by evaporating the solvent to dryness.

The 2-phenylsemicarbazides of Formula I wherein $R^3$ is acyl are prepared by treating a 2-phenylsemicarbazide wherein $R^3$ is hydrogen with an acylating agent, such as an organic acid $R^4COOH$, an acyl halide $R^4C(=O)$-halogen, or an acyl anhydride $(R^4-C(=O)-)_2O$ where $R^4$ is as defined above, either in the presence of a non-hydroxylic organic solvent such as tetrahydrofuran, diethyl ether, acetonitrile, or dioxane, or in the absence of a solvent. When a solvent is used, the concentration of reactants in the solvent should be from about 5 to about 50% preferably from 10 to 20%, to insure good mixing and at the same time keep the reaction time from being unduly lengthened because of two dilute reaction mixtures. The reaction should be carried out at a temperature of from about 10° to about 100° and preferably from 20° to 40°.

It is ordinarily preferred to have at least one molar equivalent of acylating agent available for each molar equivalent of semicarbazide to be acylated. In order to insure that the reaction proceeds to completion, it is preferable to have about 1.1 to 1.5 molar equivalents of acylating agent for each molar equivalent of semicarbazide. While it is possible to use an even greater excess of acylating agent, no particular advantages result therefrom.

Any suitable conventional method can be used to recover the acylated 2-phenylsemicarbazide, for example, evaporation of the solvent, extraction of product followed by distillation of the solvent, and the like.

When an acid halide is used as the acylating agent, it is preferable to have a tertiary amine present in a molar ratio of about 1.0 to 1.1 with respect to the acid halide. The tertiary amine, such as pyridine or triethylamine, acts as an acceptor for the hydrogen halide generated as a by-product of the reaction.

1-Alkylated-2-phenylsemicarbazides are prepared by treating a 1-acylated-2-phenylsemicarbazide with an alkylating agent, such as an alkyl halide, in the presence of a base such as triethylamine, collidine, picoline, pyridine, and the like, in an aqueous or non-aqueous reaction system, such as aqueous ethanol, acetone, dioxane, or tetrahydrofuran. The resultant product is a 1-alkylated-1-acylated-2-phenylsemicarbazide of the formula

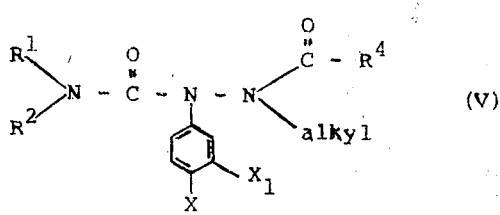

where $R^1$, $R^2$, X and $R^4$ are as defined above. The solution is then directly treated with an aqueous solution of 2.5 to 25% sodium hydroxide in an amount sufficient to provide at least one mole and preferably 1.1 to 1.5 moles of sodium hydroxide for each mole of semicarbazide to yield.

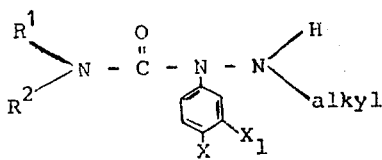

Both steps of the reaction are carried out at a temperature of from about 10° to about 100°, and preferably at 20° to 80°.

To insure the alkylation reaction proceeds to completion, it is preferred to have at least equimolar quantities of the acylated semicarbazone and the alkylating agent. The mole ratio of alkylating agent to acylated semicarbazone may be as high as 2:1 or more but no particular advantage results therefrom. Particularly preferred is the mole ratio between about 1.1:1 to 1.5 to 1.

The reaction can be carried out at sub- or super-atmospheric pressure; however, it is easier and more convenient to use atmospheric pressure. The time for the reaction to run to completion varies from about 0.5 to about 6 hrs.

The 2-phenylsemicarbazides of this invention may be easily converted to their organic or inorganic salts by reaction with the appropriate salt in an aqueous or non-aqueous reaction system.

Compounds of this invention, for example, 4,4-dimethyl-2-(3-trifluoromethyl)phenyl)semicarbazide 2-(3,4-dichlorophenyl)-4,4-dimethylsemicarbazide, and their acid addition salts have been found to be active herbicides of a general type. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes herbicidal compositions comprising a carrier or a surface-active agent, or both a carrier and a surface-active agent, and as active ingredient, at least one 2-phenylsemicarbazide or salt thereof. Likewise, the invention also includes a method of combatting weeds which comprises applying to the locus a herbicidally effective amount of a 2-phenylsemicarbazide or composition of the invention.

The term "carrier" as used herein means a solid or fluid material which may be inorganic or organic and of synthetic or natural origin with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs; magnesium aluminum silicates, for example, attapulgites and vermiculities; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers; solid polychlorophenols; bitumen, waxes, such as for example, beeswax, paraffin wax and chlorinated mineral waxes; and solid fertilizers, for example, superphosphates.

Examples of suitable fluid carriers are water, alcohols, such as for example, isopropanol, glycols; ketones, such as for example, acetone, methyl ethyl ketone, methyl isobutyl ketone and cyclohexanone; ethers; aromatic hydrocarbons, such as for example, benzene, toluene and xylene; petroleum fractions, such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonates castor oil, and sodium alkylaryl sulfonates such as sodium dodecylbenzene sulfonate; and copolymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier 3–10% by weight of a dispersing agent and, where necessary, 0-10% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½ – 10% by weight of toxicant. Granules are usually prepared to have a size between 10 and 100 BS mesh (1.676 – 0.152 mm), and may be manufactured by agglomeration or impregnation techniques. Generally granules will contain ½ – 25% by weight toxicant and 0 – 10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5 – 15% w of dispersing agents, 0.1 – 10% w of suspending agents such as protective colloids and thixotropic agents, 0 – 10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal, properties.

The method of applying the compositions of this invention comprises applying a 2-phenylsemicarbazide of Formula I, or salt thereof, ordinarily in a herbicidal composition of one of the aforementioned types to a locus or area to be protected from undesirable plant growth. the active compound, of course, is applied in amounts sufficient to exert the desired herbicidal action.

The amount of the 2-phenylsemicarbazide, or salt thereof, to be used in controlling undesirable vegetation will naturally depend on the condition of the vegetation, the degree of herbicidal activity desired, the formulation used, the mode of application, the climate, the season of the year, and other variables. Recommendations as to precise amounts are, therefore, not possible. In general, however, application to the locus to be protected of from 0.1 to 10.0 pounds per acre of the herbicidal compounds used in this invention will be satisfactory.

The preparation and some of the properties of the novel 2-phenylsemicarbazides and salts of the invention are illustrated by the following examples. It should be understood, however, that the examples given are for the purpose of illustration only, and are not to be regarded as limiting the invention in any way. In the examples below, the structure of all the products prepared was confirmed by elemental, nuclear magnetic resonance, and infrared analyses.

EXAMPLE 1 a. To a solution of 3.0 grams of 4,4-dimethyl-2-(3-trifluoromethoxyphenyl)semicarbazide hydrochloride (prepared in Example 16 below) in 25 milliliters of water was added 1.1 grams of benzaldehyde dissolved in 5 milliliters of methanol. This mixture was stirred for 2 hours and extracted with ether. The ether was evaporated to dryness and the residue was purified by silica chromatography to give 3.3 grams of viscous oil, representing a 94% yield of benzaldehyde, 4,4-dimethyl-2-(3-trifluoromethoxyphenyl)semicarbazone.

b. A mixture of 34.0 grams of benzaldehyde, 4,4-dimethyl-2-(3-trifluoromethoxyphenyl)semicarbazone (prepared in a) above) in 400 milliliters of 6% aqueous hydrochloric acid and 100 milliliters of ethylene glycol was heated to the boiling point while steam was passed into the stirred reaction mixture for 6.5 hours to remove the benzaldehyde azeotropically. The reaction mixture was cooled to 10°C and made alkaline by the addition of 30% aqueous sodium hydroxide solution. Extraction with ether gave 21.0 grams of light brown viscous liquid, representing an 82% yield of 4,4-dimethyl-2-(3-trifluoromethoxyphenyl)semicarbazide.

EXAMPLES 2–6

Using the experimental procedure of Example 1, the compounds of Table I were prepared.

TABLE I

2-Phenylsemicarbazides

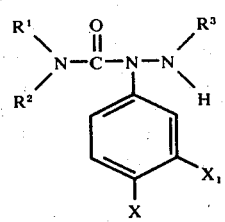

| Example Number | R¹ | R² | R³ | X | Yield % | Melting point, degrees C |
|---|---|---|---|---|---|---|
| 2 | H | H | H | 3,4-Cl₂ | 46 | 164–167 |
| 3 | H | CH₃ | H | 3,4-Cl₂ | 50 | 161–163 |
| 4 | CH₃ | CH₃ | H | 3,4-Cl₂ | 88 | 72–73 |
| 5 | CH₃ | CH₃ | CH₃ | 3,4-Cl₂ | 32 | 64–66 |

TABLE I-continued

2-Phenylsemicarbazides

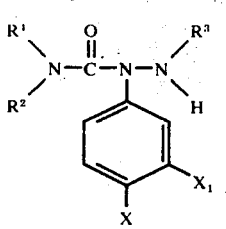

| Example Number | R¹ | R² | R³ | X | Yield % | Melting point, degrees C |
|---|---|---|---|---|---|---|
| 6 | CH₃ | CH₃ | H | 3-CF₃ | 95 | (a) |

(a) Highly viscous pale yellow liquid which shows no tendency to crystallize

EXAMPLE 7 a. A solution of 95 grams of benzaldehyde, 2-(3-chloro-4-fluoro-phenyl)-4,4-dimethylsemicarbazone and 1 liter of 10% hydrochloric acid was steam distilled until there was no detectable benzaldehyde in the distillate. The aqueous residue was cooled, treated with activated charcoal and filtered through celite. The straw yellow filtrate was concentrated to 300 milliliters. This residue was chilled in an ice bath and a portion filtered. The solid 4,4-dimethyl-2-(3-chloro-4-fluoro-phenyl)semicarbazide hydrochloride was dried in a vacuum oven.

b. The remainder of the products were made basic by addition of sodium hydroxide and extracted with ether. The ethered fractions were dried (Mg₂SO₄), filtered and concentrated to dryness. Fifty grams of off-white solid remained. The 4,4-dimethyl-2-(3-chloro-4-fluoro-phenyl)semicarbazide had a melting point of 86°–89°.

EXAMPLE 8

Using the experimental procedure of Example 7,
a. 4-methoxy-4-methyl-2-(4-chloro-3-(trifluoromethyl)phenyl)-semicarbazide hydrochloride melting point 179°–182°, and
b. the corresponding free semicarbazide, an amber syrup, were prepared.

EXAMPLE 9

Using the experimental procedure of Example 7, (a) 4,4-dimethyl-2-(4-chloro-3-(trifluoromethyl)phenyl)-semicarbazide hydrochloride, melting point 200°–203°, and (b) the corresponding free semicarbazide, were prepared.

EXAMPLE 10

Using the experimental procedure of Example 7, (a) 4,4-dimethyl-2-(4-fluoro-3-(trifluoromethyl)phenyl)-semicarbazide hydrochloride, melting at 168°–171°, and (b) the corresponding free semicarbazide, an amber syrup, were prepared.

EXAMPLE 11

Using the experimental procedure of Example 7, (a) 4-methoxy-4-methyl-2-(4-fluoro-3-(trifluoromethyl)-phenyl)-semicarbazide hydrochloride, melting point 165°–168°, and (b) the corresponding free semicarbazide (72.4% yield) a light amber oil were prepared.

EXAMPLE 12

Using the procedure of Example 12, 2-(3,4-dichlorophenyl)-4,4-dimethyl-1-(trifluoroacetyl)semicarbazide, melting at 146°–148°C, was prepared in 29% yield.

EXAMPLE 13

Using the procedure of Example 12, 4,4-dimethyl-1-trifluoroacetyl-2-(3-trifluoromethylphenyl)semicarbazide, melting at 118°–121°C, was prepared in 19% yield.

EXAMPLE 14 a. To a stirred solution of 72 grams of benzaldehyde, (3,4-dichlorophenyl)hydrazone in 450 milliliters of dimethylformamide was added portionwise 9.2 grams of sodium hydride. This addition was exothermic to 50°C. After the vigorous evolution of hydrogen had ceased, the solution was cooled to 25°C while 46.0 grams of dimethylcarbamoyl chloride was added dropwise with stirring. This addition was exothermic to 45°C. After 12 hours, the reaction mixture was poured into 2500 milliliters of ice water and extracted with ether. The ether extracts were washed with water, dried, and concentrated to dryness. The residual solid was recrystallized from a 10 to 1 mixture of hexane and ether to give 77.6 grams of a tan solid melting at 94°–95°C, representing an 85% yield of benzaldehyde, 2-(3,4-dichlorophenyl)-1,1-dimethylsemicarbazone.

b. A mixture of 10.1 grams of benzaldehyde, 2-(3,4-dichlorophenyl)-1,1-dimethylsemicarbazone (prepared in (a) above), 25 milliliters of isopropanol, 250 milliliters of water, and 15 milliliters of concentrated hydrochloric acid was heated with stirring while steam was passed through the mixture in order to remove by-product benzaldehyde azeotropically. After 3 hours, the reaction mixture was cooled to 20°C and extracted with ether. The aqueous phase was concentrated to 75 milliliters and cooled to 5°C. Filtration gave 6.95 grams of colorless crystalline solid melting at 188°–190°C, representing an 81% yield of 2-(3,4-dichlorophenyl)-4,4-dimethylsemicarbazide hydrochloride.

EXAMPLE 15

Using the experimental procedure of Example 14, 4,4-dimethyl-2-(3-trifluoromethylphenyl)semicarbazide hydrochloride melting at 187°–189°C was prepared in 84% yield.

EXAMPLE 16

Following the experimental procedure of Example 14, 4,4-dimethyl-2-(3-trifluoromethoxyphenyl)-semicarbazide hydrochloride melting at 152°–153°C was prepared in 92% yield.

EXAMPLE 17

The pre-emergence herbicidal activity of the compounds of the invention was evaluated by planting seeds of watergrass and cress in soil treated with the test compounds at the rate of 25 and 2.5 pounds per acre. The planted soil was held under controlled conditions of temperature, moisture, and light for 13 to 14 days. The amount of germination was then noted and the effectiveness of the test compound was rated on the basis of an 0 to 9 scale, 0 rating indicating no effect, 9 indicating death of the seedlings or no germination.

The post-emergence activity of the comounds of this invention was evaluated by spraying 10-day old pigweed plants and 7-day old crabgrass plants with a liquid formulation of the test compound at the rate of 10 pounds and 1 pound per acre. The sprayed plants were held under controlled conditions for 10 to 11 days and the effect of the test chemical then evaluated visually, the results being rated on the 0 to 9 scale described above.

The general phytotoxicity of the compounds was evaluated by planting ryegrass and sowthistle plants in culture solutions treated with the test compounds at the rate of 10 parts and 1 part per million solution. The plants were held under controlled conditions for 10 to 11 days. The amount of growth of the roots and shoots was noted, and the effectiveness of the test compound rated on the 0 to 9 scale described above wherein 9 indicates death of the plant.

The results of the tests are summarized in Table II and Table III.

TABLE II

Herbicidal Activity

| Compound of Example | Pre-emergence | | | | Post-emergence | | | | General | | | | | | | |
|---|---|---|---|---|---|---|---|---|---|---|---|---|---|---|---|---|
| | Watergrass | | Cress | | Crabgrass | | Pigweed | | Ryegrass | | | | Sowthistle | | | |
| | | | | | | | | | Roots | | Shoots | | Roots | | Shoots | |
| | 25 lbs/acre | 2.5 lbs/acre | 25 lbs/acre | 2.5 lbs/acre | 10 lbs/acre | 1 lbs/acre | 10 lbs/acre | 1 lbs/acre | 10* | 1* | 10* | 1* | 10* | 1* | 10* | 1* |
| 6 | 9 | 7 | 9 | 9 | 9 | 7 | 0 | 0 | 8 | 4 | 8 | 2 | 9 | 3 | 9 | 6 |
| 6 | 9 | 7 | 9 | 9 | 9 | 4 | 7 | 0 | 7 | 3 | 7 | 4 | 9 | 0 | 9 | 2 |
| 1 | 9 | 6 | 9 | 9 | 9 | 0 | 0 | 0 | 9 | 0 | 8 | 3 | 9 | 6 | 9 | 7 |
| 1 | 9 | 6 | 9 | 9 | 9 | 4 | 7 | 3 | 7 | 2 | 7 | 2 | 7 | 0 | 8 | 2 |
| 4 | 8 | 6 | 9 | 9 | 9 | 9 | 9 | 9 | 9 | 9 | 8 | 8 | 9 | 9 | 9 | 9 |
| 7(b) | 8 | 6 | 9 | 9 | 9 | 9 | 9 | 9 | — | — | — | — | — | — | — | — |
| 16 | 9 | 6 | 9 | 7 | 9 | 0 | 6 | 0 | 7 | 0 | 6 | 0 | 7 | 4 | 8 | 7 |
| 16 | 9 | 6 | 9 | 9 | 9 | 0 | 3 | 2 | 9 | 2 | 8 | 2 | 9 | 0 | 9 | 1 |
| 15 | 9 | 6 | 9 | 9 | 9 | 8 | 6 | 0 | 7 | 5 | 7 | 4 | 7 | 5 | 8 | 7 |
| 14 | 9 | 8 | 9 | 9 | 9 | 6 | 9 | 5 | 8 | 8 | 8 | 8 | 8 | 2 | 8 | 7 |
| 3 | 6 | 4 | 9 | 7 | 9 | 5 | 9 | 0 | 9 | 7 | 8 | 7 | 9 | 7 | 8 | 7 |
| 5 | 7 | 3 | 9 | 9 | 9 | 9 | 9 | 7 | 6 | 6 | 9 | 8 | 9 | 6 | 9 | 8 |
| 5 | 8 | 2 | 9 | 9 | 9 | 9 | 9 | 8 | 9 | 8 | 8 | 8 | 9 | 7 | 8 | 8 |
| 12 | 7 | 2 | 8 | 7 | 9 | 4 | 9 | 0 | 9 | 0 | 8 | 2 | 9 | 8 | 9 | 8 |

*parts/million
— indicates no test

TABLE III

Herbicidal Activity

| Compound of Example | Pre-emergence | | | | | | | | | Post-emergence | | | | | | | | |
|---|---|---|---|---|---|---|---|---|---|---|---|---|---|---|---|---|---|---|
| | Watergrass | | Cress | | Soybean | | G.Sorgh. | | Cotton | Crabgrass | | Pigweed | | Soybean | | G. Sorgh. | Cotton |
| | 2.5 lbs/acre | 25 lbs/acre | 2.5 lbs/acre | 25 lbs/acre | 2.5 lbs/acre | 25 lbs/acre | 2.5 lbs/acre | 25 lbs/acre | 25 lbs/acre | 1* | 10* | 1* | 10* | 1* | 10* | 1* | 10* | 10* |
| 11(b) | 4 | 9 | 9 | 9 | — | 7 | — | 8 | 2 | 0 | 5 | 0 | 4 | — | 2 | — | 0 | 0 |
| 11(a) | 1 | 8 | 7 | 9 | — | 9 | — | 9 | 8 | 0 | 1 | 0 | 1 | — | 0 | — | 0 | 0 |
| 10(b) | 6 | 7 | 9 | 9 | — | 9 | — | 7 | 3 | 2 | 5 | 0 | 8 | — | 4 | — | 6 | 0 |
| 10(a) | 6 | 7 | 8 | 9 | — | 2 | — | 1 | 0 | 1 | 7 | 6 | 9 | — | 8 | — | 8 | 7 |
| 9(b) | 6 | 7 | 9 | 9 | — | 7 | — | 0 | 1 | 1 | 9 | 3 | 9 | — | 5 | — | 6 | 0 |
| 8(b) | 0 | 7 | 8 | 9 | — | 7 | — | 0 | 1 | 0 | 7 | 0 | 3 | — | 5 | — | 6 | 0 |
| 9(a) | 6 | 7 | 9 | 9 | — | 8 | — | 5 | 2 | 7 | 8 | 4 | 9 | — | 4 | — | 9 | 2 |
| 8(a) | 0 | 6 | 9 | 9 | — | 3 | — | 5 | 1 | 0 | 7 | 0 | 6 | — | 2 | — | 1 | 0 |

*parts/million
— indicates no test

EXAMPLE 18

The pre-emergence herbicidal effect of the compounds of the invention was further tested on eight weeds. The results of the pre-emergence tests are given in Table IV.

TABLE IV

Pre-emergence Herbicide/Plant - $LD_{90}$ (lb/acre)

| Compound of Example | Ryegrass | Cheat-grass | Crabgrass | Watergrass | Pigweed | Mustard | Sowthistle | Curly Dock |
|---|---|---|---|---|---|---|---|---|
| 16[3] | | 4.5 | 3.5 | 2.5 | 6.0 | 0.45 | 1.3 | 1.0 | 2.5 |
| 16[4] | | 1.5 | 0.6 | 0.6 | 2.5 | 1.0 | 0.45 | 0.9 | 0.8 |
| 14[3] | | 0.9 | 1.2 | 0.7 | 1.7 | 0.4 | 0.45 | 0.4 | 0.4 |
| 7(b)[4] | — | <0.5[1] | <0.5 | 1.6 | <0.5 | 1.4 | — | <0.5 |
| 4[3] | <0.5 | 2.5 | 0.8 | 1.7 | <0.5 | <0.5 | <0.5 | <0.5 |
| 6[3] | 2.5 | 1.8 | 1.2 | 3.5 | .6 | .6 | .8 | 1.3 |
| 6[4] | .6 | .45 | .35 | .8 | .45 | .21 | .25 | .45 |
| 5 | 1.1 | 2.0 | <0.5 | 1.0 | <0.5 | <0.5 | — | <0.5 |
| 3 | >5.0[2] | >5.0 | >5.0 | >5.0 | 4.6 | >5.0 | — | >5.0 |
| 12 | 2.3 | 4.6 | 2.0 | >5.0 | 2.0 | 2.3 | 2.3 | 1.3 |

TABLE IV-continued

| Compound of Example | Pre-emergence Herbicide Plant - LD$_{95}$ (lb/acre) | | | | | | | |
|---|---|---|---|---|---|---|---|---|
| | Ryegrass | Cheatgrass | Crabgrass | Watergrass | Pigweed | Mustard | Sowthistle | Curly Dock |
| 2[4] | — | >2.8 | >2.8 | >2.8 | >2.8 | >2.8 | — | >2.8 |

[1]The symbol < means "less than".
[2]The symbol > means "more than".
[3]Testing done on Nicollet soil.
[4]Testing done on Hanford
— indicates no test

I claim as my invention:

1. A compound having the formula

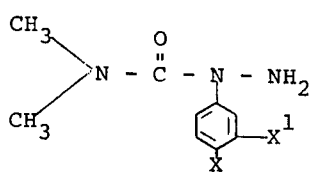

wherein X and X$^1$ each is halogen of atomic number 9–35, inclusive, or an acid addition salt thereof.

2. A compound according to claim 1 wherein X and X$^1$ are chlorine.

3. A compound according to claim 1 wherein X is fluorine and X$^1$ is chlorine.

4. A compound having the formula

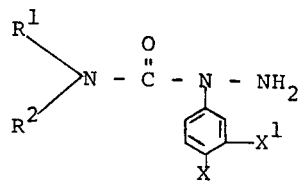

wherein R$^1$ and R$^2$ each is alkyl of 1 to 4 carbon atoms, X is hydrogen and X$^1$ is trifluoromethyl or an acid addition salt thereof.

5. A compound according to claim 4 wherein R$^1$ and R$^2$ each is methyl.

* * * * *

UNITED STATES PATENT AND TRADEMARK OFFICE
CERTIFICATE OF CORRECTION

PATENT NO. : U.S. 3,984,463
DATED : October 5, 1976
INVENTOR(S) : KURT H. G. PILGRAM It is certified that error appears in the above-identified patent and that said Letters Patent are hereby corrected as shown below:

Page 1, under References cited,

"7,110,689" should read -- 7,010,689 --.

Signed and Sealed this

Nineteenth Day of April 1977

[SEAL]

Attest:

RUTH C. MASON
*Attesting Officer*

C. MARSHALL DANN
*Commissioner of Patents and Trademarks*